(12) United States Patent
Kimura et al.

(10) Patent No.: US 9,850,209 B2
(45) Date of Patent: Dec. 26, 2017

(54) METHOD FOR MANUFACTURING 3-(ALKYLSULFONYL)PYRIDINE-2-CARBOXYLIC ACID

(71) Applicant: SUMITOMO CHEMICAL COMPANY, LIMITED, Tokyo (JP)

(72) Inventors: Takahiro Kimura, Takarazuka (JP); Ryota Maehata, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/318,517

(22) PCT Filed: Jun. 22, 2015

(86) PCT No.: PCT/JP2015/067828
§ 371 (c)(1),
(2) Date: Dec. 13, 2016

(87) PCT Pub. No.: WO2015/199007
PCT Pub. Date: Dec. 30, 2015

(65) Prior Publication Data
US 2017/0166529 A1 Jun. 15, 2017

(30) Foreign Application Priority Data
Jun. 26, 2014 (JP) .................. 2014-131041

(51) Int. Cl.
*C07D 213/81* (2006.01)
*C07D 213/803* (2006.01)

(52) U.S. Cl.
CPC ....... *C07D 213/81* (2013.01); *C07D 213/803* (2013.01)

(58) Field of Classification Search
None
See application file for complete search history.

(56) References Cited

U.S. PATENT DOCUMENTS

2009/0111791 A1   4/2009   De Lombaert et al.

FOREIGN PATENT DOCUMENTS

| CH | 657124 A5 | 8/1986 |
|----|-----------|--------|
| WO | WO 2013/018928 A1 | 2/2013 |
| WO | WO 2014/104407 A1 | 7/2014 |

OTHER PUBLICATIONS

Miletin et al, 2nd International Electronic Conference on Synthetic Organic Chemistry (ECSOC-2), Sep. 1-30, 1998.*

Blank et al., "Mercapto Heterocyclic Carboxylic Acids, Analogues of 3-Mercaptopicolinic Acid", Journal of Medicinal Chemistry, vol. 20, No. 4, 1977, pp. 572-576.
Blank et al., "Mercaptopyridinecarboxylic Acids, Synthesis and Hypoglycemic Activity", Journal of Medicinal Chemistry, vol. 17, No. 10, 1974, pp. 1065-1071.
International Preliminary Report on Patentability and Translation of the Written Opinion of the International Searching Authority (Forms PCT/IB/373 and PCT/ISA/237), dated Dec. 27, 2016, for International Application No. PCT/JP2015/067828.
International Search Report (Form PCT/ISA/210), dated Sep. 1, 2015, for International Application No. PCT/JP2015/067828, including an English Translation.

* cited by examiner

*Primary Examiner* — Zinna Northington Davis
(74) *Attorney, Agent, or Firm* — Birch, Stewart, Kolasch & Birch, LLP

(57) ABSTRACT

A 3-(alkylsulfonyl)pyridine-2-carboxylic acid or a salt thereof can be manufactured by comprising:
allowing a compound represented by formula (1-N):

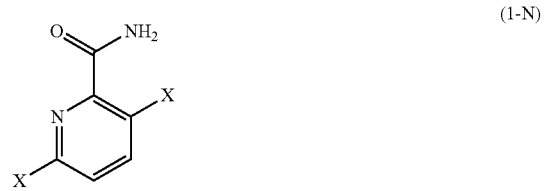

(1-N)

wherein X represents a halogen atom,
to react with a compound represented by formula (2):

$$R^2SM^2 \quad (2)$$

wherein $R^2$ represents a $C_{1-8}$ straight-chain alkyl group, and $M^2$ represents a hydrogen atom or an alkali metal,
to give a compound represented by formula (3-N):

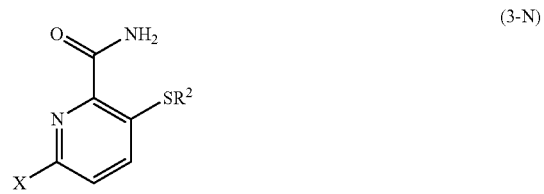

(3-N)

wherein $R^2$ and X are as defined above;
allowing the compound (3-N) to react with hydrogen peroxide in the presence of a tungsten catalyst and an acid;
reducing the product in the presence of a base and a heterogeneous transition metal catalyst;
and hydrolyzing the product in the presence of a base.

6 Claims, No Drawings

METHOD FOR MANUFACTURING 3-(ALKYLSULFONYL)PYRIDINE-2-CARBOXYLIC ACID

TECHNICAL FIELD

The present invention relates to a method for producing a 3-(alkylsulfonyl)pyridine-2-carboxylic acid.

BACKGROUND ART

A 3-(alkylsulfonyl)pyridine-2-carboxylic acid is an important compound that serves as an intermediate in the production of pharmaceuticals and agrochemicals (e.g., WO 2013/018928), and various production methods are known.

Journal of Medicinal Chemistry, 1974, Vol. 17, No. 10, pp. 1065-1071, describes a method for producing 3-(methylthio)pyridine-2-carboxylic acid from 3-aminopicolinic acid, and Journal of Medicinal Chemistry, 1977, Vol. 20, No. 4, pp. 572-576, describes a method in which 3-(methylthio)pyridine-2-carboxylic acid is converted into a methyl ester, oxidized, and then hydrolyzed to produce 3-(methylsulfonyl)pyridine-2-carboxylic acid.

Meanwhile, for a method of producing a 3-(alkylthio)pyridine-2-carboxylic acid, a production method in which 3-halogenopyridine-2-carboxylic acid is allowed to react with a thiol compound is known (WO 2013/018928).

SUMMARY OF INVENTION

The present invention provides a method for producing a 3-(alkylsulfonyl)pyridine-2-carboxylic acid from 3,6-dihalogenopyridine-2-carboxylic acid.

According to the present invention, a compound represented by the below formula (7) or a salt thereof can be produced by a production method comprising:

Step AN of allowing a compound represented by formula (1-N):

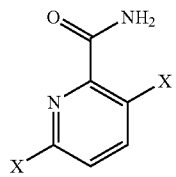

(1-N)

(wherein X represents a halogen atom)
to react with a compound represented by formula (2):

$$R^2SM^2 \quad (2)$$

(wherein $R^2$ represents a $C_{1-8}$ straight-chain alkyl group, and $M^2$ represents a hydrogen atom or an alkali metal)
to give a compound represented by formula (3-N):

(3-N)

(wherein $R^2$ and X are as defined above);
Step CN of allowing the compound represented by formula (3-N) to react with hydrogen peroxide in the presence of a tungsten catalyst and an acid to give a compound represented by (6-N):

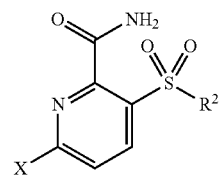

(6-N)

(wherein $R^2$ and X are as defined above);
Step DN of reducing the compound represented by formula (6-N) in the presence of a base and a heterogeneous transition metal catalyst to give a compound represented by formula (8-N):

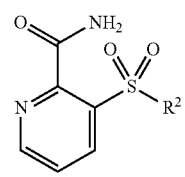

(8-N)

(wherein $R^2$ is as defined above); and
Step EN of hydrolyzing the compound represented by formula (8-N) in the presence of a base to give a compound represented by formula (7) or a salt thereof:

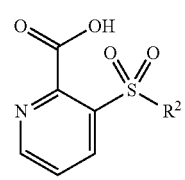

(7)

(wherein $R^2$ is as defined above).

MODE FOR CARRYING OUT THE INVENTION

Hereinafter, the present invention will be described in detail.

$C_{1-8}$ straight-chain alkyl group is a methyl group, an ethyl group, a propyl group, a butyl group, an octyl group, or the like.

Halogen atom is a fluorine atom, a chlorine atom, a bromine atom, or an iodine atom.

Alkali metal means lithium, sodium, potassium, cesium, or the like.

Step AN is a step of allowing a compound represented by formula (1-N) (hereinafter referred to as compound (1-N)) to react with a compound represented by formula (2) (hereinafter referred to as compound (2)) to produce a compound represented by formula (3-N) (hereinafter referred to as compound (3-N)).

In compound (1-N), two Xs represent the same atoms, and are preferably chlorine atoms.

Examples of compound (1-N) include 3,6-dichloropyridine-2-carboxamide and 3,6-dibromopyridine-2-carboxamide.

Compound (1-N) can be produced by the reaction between the corresponding carboxylic acid halide and ammonia. The carboxylic acid halide can be produced by halogenating the corresponding carboxylic acid with an acid halide or the like.

In compound (2), $R^2$ is preferably a $C_{1-4}$ straight-chain alkyl group, and more preferably a methyl group or an ethyl group. M is preferably a hydrogen atom, sodium, or potassium.

Examples of compound (2) include alkanethiols such as methanethiol, ethanethiol, propanethiol, butanethiol, and octanethiol; and alkali metal alkanethiolates such as lithium methanethiolate, sodium methanethiolate, potassium methanethiolate, lithium ethanethiolate, sodium ethanethiolate, potassium ethanethiolate, lithium propanethiolate, sodium propanethiolate, potassium propanethiolate, lithium butanethiolate, sodium butanethiolate, and potassium butanethiolate. Preferred are methanethiol, ethanethiol, sodium methanethiolate, potassium methanethiolate, sodium ethanethiolate, and potassium ethanethiolate.

In Step AN, in the case where an alkanethiol, such as methanethiol or ethanethiol, is used as compound (2), the step is usually performed in the presence of a base. Examples of the base include alkali metal hydrides such as lithium hydride, sodium hydride, and potassium hydride; alkali metal hydroxides such as lithium hydroxide, sodium hydroxide, and potassium hydroxide; alkaline earth metal hydroxides such as calcium hydroxide and barium hydroxide; and alkali metal alcoholates such as lithium methylate, sodium methylate, potassium methylate, lithium ethylate, sodium ethylate, potassium ethylate, lithium tert-butyrate, sodium tert-butyrate, and potassium tert-butyrate. Preferred are sodium hydride, potassium hydride, sodium hydroxide, potassium hydroxide, sodium methylate, potassium methylate, sodium ethylate, potassium ethylate, sodium tert-butyrate, and potassium tert-butyrate.

The reaction is usually carried out in a solvent. Examples of the solvent include aromatic hydrocarbon solvents such as toluene, xylene, and ethylbenzene, halogenated aromatic hydrocarbon solvents such as monochlorobenzene and o-dichlorobenzene, ether solvents such as tetrahydrofuran and methyl tert-butyl ether, nitrile solvents such as acetonitrile and propionitrile, ester solvents such as ethyl acetate and propyl acetate, halogenated hydrocarbon solvents such as dichloromethane and 1,2-dichloroethane, amide solvents such as N,N-dimethylformamide, N,N-dimethylacetamide, and N-methylpyrrolidone, water, and mixed solvents thereof.

Step AN is usually performed by mixing compound (1-N) and compound (2). For mixing, compound (2) may be added to compound (1-N), or compound (1-N) may be added to compound (2).

In the case of using a base, a method in which compound (1-N) is added to a mixture of compound (2) and a base, a method in which a mixture of compound (2) and a base is added to compound (1-N), and a method in which a base is added to a mixture of compound (1-N) and compound (2) can be mentioned.

The amount of compound (2) used is usually 0.8 to 3.0 times, preferably 1.0 to 1.5 times by mole of compound (1-N).

The amount of the base used is usually 0.8 to 3.0 times, preferably 0.9 to 1.2 times by mole of compound (2).

In the case where the reaction mixture separates into an organic layer and an aqueous layer, a phase transfer catalyst may be used. Examples of the phase transfer catalyst include quaternary ammonium salts such as tetrabutylammonium bromide, tetrabutylammonium chloride, tetrabutylammonium hydroxide, benzyltrimethylammonium bromide, benzyltrimethylammonium chloride, and benzyltrimethylammonium hydroxide; and phosphonium salts such as tetrabutylphosphonium chloride, tetrabutylphosphonium bromide, tetrabutylphosphonium hydroxide, tetraphenylphosphonium bromide, and tetraphenylphosphonium chloride.

The amount of the phase transfer catalyst used is usually 0.01 to 1.0 time, preferably 0.02 to 0.3 times by mole of compound (2).

The reaction temperature is usually −10 to 100° C., preferably 0 to 60° C. The reaction time depends on the reaction temperature, and is usually 1 to 50 hours.

After the completion of the reaction, water is added to the reaction mixture, followed by extraction with an organic solvent, and the obtained organic layer is concentrated, whereby compound (3-N) can be isolated. The obtained compound (3-N) may be further purified by column chromatography or recrystallization.

Typical examples of compound (3-N) include 6-chloro-3-(methylthio)pyridine-2-carboxamide, 6-chloro-3-(ethylthio)pyridine-2-carboxamide, 6-chloro-3-(propylthio)pyridine-2-carboxamide, 6-chloro-3-(butylthio)pyridine-2-carboxamide, 6-bromo-3-(methylthio)pyridine-2-carboxamide, 6-bromo-3-(ethylthio)pyridine-2-carboxamide, 6-bromo-3-(propylthio)pyridine-2-carboxamide, and 6-bromo-3-(butylthio)pyridine-2-carboxamide.

Step CN is a step of allowing compound (3-N) to react with hydrogen peroxide in the presence of a tungsten catalyst and an acid to produce a compound represented by formula (6-N) (hereinafter referred to as compound (6-N)).

Hydrogen peroxide is usually used in the form of an aqueous solution, and the concentration is usually 10 to 70 wt %, preferably 30 to 60 wt %.

The amount of the hydrogen peroxide used is usually 1.5 to 5 times, preferably 2.0 to 3.0 times by mole of compound (3-N).

Examples of the tungsten catalyst include tungsten, tungstic acid, sodium tungstate, tungsten oxide, sodium phosphotungstate, and silicotungstic acid, and sodium tungstate is preferable.

The amount of the tungsten catalyst used is usually 0.5 to 10 mol, preferably 1.0 to 5.0 mol, per 100 mol of compound (3-N).

Examples of the acid include water-soluble acids such as sulfuric acid, methanesulfonic acid, ethanesulfonic acid, nitric acid, and phosphoric acid, and sulfuric acid is preferable.

The amount of the acid used is usually 0.01 to 1 times, preferably 0.05 to 0.2 times by mole of compound (3-N).

Step CN is usually performed in a solvent. For the solvent, water or a mixed solvent of water and an organic solvent is used. Examples of the organic solvent include aromatic hydrocarbon solvents such as toluene, xylene, and ethylbenzene; halogenated aromatic hydrocarbon solvents such as monochlorobenzene and o-dichlorobenzene; ether solvents such as tetrahydrofuran and methyl tert-butyl ether; nitrile solvents such as acetonitrile and propionitrile; ester solvents such as ethyl acetate and propyl acetate; halogenated hydrocarbon solvents such as dichloromethane and 1,2-dichloroethane; and amide solvents such as N,N-dimethylformamide, N,N-dimethylacetamide, and N-methylpyrrolidone.

Step CN is usually performed by mixing compound (3-N), hydrogen peroxide, an acid, and a tungsten catalyst.

For a general mixing method, hydrogen peroxide is added to a mixture of compound (3-N), a tungsten catalyst, an acid, and water.

Step CN may also be performed in the presence of a sodium salt of ethylenediaminetetraacetic acid. The amount used is usually 0.8 to 1.5 times by mole of the tungsten catalyst.

The reaction temperature is usually 10 to 100° C., preferably 40 to 90° C. The reaction time depends on the reaction temperature, and is usually 1 to 50 hours.

After the completion of the reaction, excess hydrogen peroxide is removed, and the precipitated solid is separated by filtration from the reaction mixture, or alternatively the reaction mixture is extracted with an organic solvent, and the obtained organic layer is concentrated, whereby compound (6-N) can be isolated. Compound (6-N) may also be further purified by recrystallization.

Examples of compound (6-N) include
6-chloro-3-(methylsulfonyl)pyridine-2-carboxamide,
6-bromo-3-(methylsulfonyl)pyridine-2-carboxamide,
6-chloro-3-(ethylsulfonyl)pyridine-2-carboxamide,
6-bromo-3-(ethylsulfonyl)pyridine-2-carboxamide,
6-chloro-3-(propylsulfonyl)pyridine-2-carboxamide,
6-bromo-3-(propylsulfonyl)pyridine-2-carboxamide,
6-chloro-3-(butylsulfonyl)pyridine-2-carboxamide, and
6-bromo-3-(butylsulfonyl)pyridine-2-carboxamide.

Step DN is a step of reducing compound (6-N) in the presence of a base and a heterogeneous transition metal catalyst to give a compound represented by formula (8-N) (hereinafter referred to as compound (8-N)).

Examples of the heterogeneous transition metal catalyst include heterogeneous palladium catalysts such as palladium/carbon, palladium/silica, palladium/alumina, and palladium/barium sulfate; heterogeneous platinum catalysts such as platinum/carbon, platinum/silica, and platinum/alumina; heterogeneous ruthenium catalysts such as ruthenium/carbon, ruthenium/silica, and ruthenium/alumina; heterogeneous rhodium catalysts such as rhodium/carbon, rhodium/silica, and rhodium/alumina; heterogeneous iridium catalysts such as iridium/carbon; heterogeneous osmium catalysts such as osmium/carbon; heterogeneous nickel catalysts such as nickel-diatomaceous earth catalysts and Raney nickel; and cobalt catalysts such as Raney cobalt catalysts. Preferred are heterogeneous platinum-group catalysts including palladium, platinum, ruthenium, rhodium, iridium, and osmium, which are platinum-group elements. Heterogeneous palladium catalysts are more preferable for industrial use, and palladium/carbon is most preferable.

The amount of the heterogeneous catalyst used is usually 0.01 to 5 mol, preferably 0.05 to 0.5 mol, per 100 mol of compound (6-N).

The base may be any base capable of neutralizing the formed hydrogen halide. Examples thereof include alkali metal carbonates such as lithium carbonate, potassium carbonate, and sodium carbonate; alkali metal hydrogen carbonates such as lithium hydrogen carbonate, sodium hydrogen carbonate, and potassium hydrogen carbonate; alkali metal carboxylates such as lithium acetate, sodium acetate, potassium acetate, lithium oxalate, sodium oxalate, and potassium oxalate; alkali metal phosphates such as lithium phosphate, sodium phosphate, and potassium phosphate; alkali metal hydrogen phosphates such as lithium hydrogen phosphate, sodium hydrogen phosphate, and potassium hydrogen phosphate; and alkali metal dihydrogen phosphates such as lithium dihydrogen phosphate, sodium dihydrogen phosphate, and potassium dihydrogen phosphate.

The amount of the base used is usually 0.3 to 3 times, preferably 0.5 to 1.5 times by mole of compound (6-N).

For the reduction reaction, a reducing agent such as hydrogen or ammonium formate is used. In the case where hydrogen is used, the hydrogen partial pressure is usually 0.01 to 5 MPa, preferably 0.05 to 1 MPa.

In the case where ammonium formate is used, the amount thereof is usually 0.8 to 5 times, preferably 1.0 to 3.0 times by mole of compound (6-N).

The reduction reaction is usually carried out in a solvent. Examples of the solvent include water; alcohol solvents such as methanol, ethanol, and 2-propanol; aromatic hydrocarbon solvents such as toluene, xylene, and ethylbenzene; ether solvents such as tetrahydrofuran and methyl tert-butyl ether; ester solvents such as ethyl acetate and propyl acetate; ketone solvents such as acetone and methyl isobutyl ketone; amide solvents such as N,N-dimethylformamide, N,N-dimethylacetamide, and N-methylpyrrolidone; and mixed solvents thereof.

Step DS is usually performed by mixing compound (6-N), a base, a heterogeneous transition metal catalyst, and a reducing agent. As a method for mixing, for example, a reducing agent is added to a mixture of compound (6-N), a base, and a heterogeneous transition metal catalyst, or compound (6-N) and a reducing agent are each added to a mixture of a base and a heterogeneous transition metal catalyst.

The reaction temperature is usually 10 to 100° C., preferably 20 to 60° C. The reaction time depends on the reaction temperature and the hydrogen partial pressure, and is usually 1 to 50 hours.

After the completion of the reaction, the solids, including the catalyst, are removed by filtration, and the filtrate is concentrated, whereby a compound represented by formula (8-N) (hereinafter referred to as compound (8-N)) can be obtained. Further, water is added, followed by extraction with an organic solvent, and the obtained organic layer is concentrated, whereby compound (8-N) can be isolated. Compound (8-N) may also be further purified by recrystallization.

Typical examples of compound (8-N) include
3-(methylsulfonyl)pyridine-2-carboxamide,
3-(ethylsulfonyl)pyridine-2-carboxamide,
3-(propylsulfonyl)pyridine-2-carboxamide, and
3-(butylsulfonyl)pyridine-2-carboxamide.

Step EN is a step of hydrolyzing compound (8-N) in the presence of a base to give a compound represented by formula (7) (hereinafter referred to as compound (7)).

Examples of the base usually used include alkali metal carbonates such as lithium carbonate, sodium carbonate, and potassium carbonate; alkali metal hydroxides such as lithium hydroxide, sodium hydroxide, and potassium hydroxide; alkaline earth metal hydroxides such as calcium hydroxide and barium hydroxide; and alkali metal alcoholates such as lithium methylate, sodium methylate, potassium methylate, lithium ethylate, sodium ethylate, and potassium ethylate. It is preferable to use sodium hydroxide or potassium hydroxide.

The amount of the base used is usually 1.0 to 10 times, preferably 1.5 to 3.0 times by mole of compound (8-N).

Step EN is usually performed in a solvent. For the solvent, water or a mixed solvent of water and an alcohol solvent, such as methanol, ethanol, or isopropyl alcohol, is usually used.

The reaction temperature is usually 10 to 150° C., preferably 50 to 90° C. The reaction time depends on the reaction temperature, and is usually 1 to 50 hours.

After the completion of the reaction, usually, compound (7) is in the form of a solution of a salt, and compound (7) can be directly isolated as a salt. It is also possible that an aqueous solution of an acid, such as hydrochloric acid or sulfuric acid, is added to the solution, and the precipitated solid is separated by filtration, or alternatively an aqueous solution of an acid, such as hydrochloric acid or sulfuric acid, is added to the solution, followed by extraction with an organic solvent, and the obtained organic layer is concentrated, thereby isolating compound (7). Compound (7) and a salt thereof may also be further purified by recrystallization. Typical examples of the salt of compound (7) include alkali metal salts such as a lithium salt, a sodium salt, and a potassium salt.

EXAMPLES

Hereinafter, the present invention will be described in detail with reference to examples. However, the present invention is not limited only to these examples.

First, a production method for compound (1-N) will be shown as a reference example.

Reference Example 1

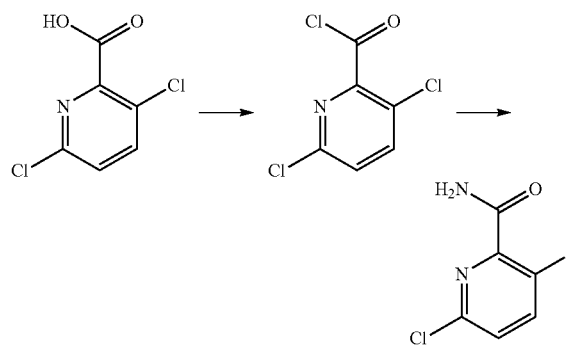

Under a nitrogen atmosphere, 17.13 g of thionyl chloride was added dropwise to a mixture of 25.0 g of 3,6-dichloropyridine-2-carboxylic acid, 125 g of toluene, and 0.48 g of N,N-dimethylformamide at 80° C. over 30 minutes. The mixture was stirred at the same temperature for 1.5 hours, cooled to 60° C., and then concentrated under reduced pressure to 26.45 g. The concentrate was added dropwise to 75 g of 28 wt % aqueous ammonia at 0° C. or less over 1 hour and stirred at room temperature for 12 hours. The precipitate was filtered, and the obtained solid was washed with 60 mL of water and then dried under reduced pressure, thereby giving 14.89 g of 3,6-dichloropyridine-2-carboxamide.

$^1$H-NMR (DMSO-$d_6$) δ: 7.65-7.67 (1H, d), 7.88 (1H, br), 8.08-8.12 (2H, m)

Example 1

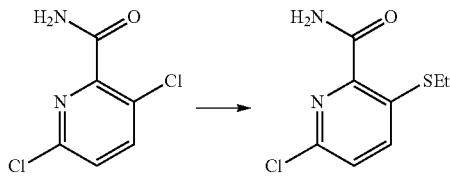

Under a nitrogen atmosphere, a mixture of 5.33 g of 28 wt % sodium methylate and 1.72 g of ethyl mercaptan was added dropwise to a mixture of 5.0 g of 3,6-dichloropyridine-2-carboxamide and 15 g of tetrahydrofuran at 0° C., and stirred at the same temperature for 5 hours and then at 20° C. for 4 hours. To the reaction mixture, 30 mL of toluene was added, and the organic layer was washed with 30 mL of water and then with 20 mL of water and concentrated under reduced pressure to give 5.37 g of a solid containing 6-chloro-3-(ethylthio)pyridine-2-carboxamide and 3-chloro-6-(ethylthio)pyridine-2-carboxamide in a ratio of 93.2/6.8.

6-Chloro-3-(ethylthio)pyridine-2-carboxamide $^1$H-NMR (DMSO-$d_6$) δ: 1.22-1.26 (3H, t), 2.90-2.95 (2H, q), 7.58-7.62 (1H, d), 7.69 (1H, br), 7.88-7.92 (1H, d), 7.96 (1H, br)

Example 2

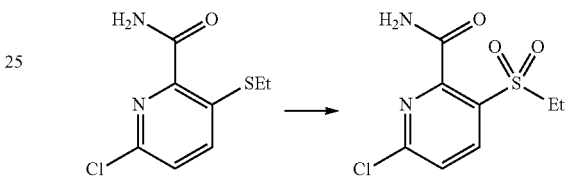

Aqueous hydrogen peroxide (2.30 g, 35.3 wt %) was added dropwise to a mixture of 2.00 g of 6-chloro-3-(ethylthio)pyridine-2-amide, 151.4 mg of sodium tungstate dihydrate, 453.0 mg of 96 wt % sulfuric acid, and 10.00 g of water at 80° C. over 1 hour. The reaction mixture was stirred at 80° C. for 1 hour and then stirred at room temperature for 1 hour. The precipitated solid was filtered, the obtained solid was washed with 2 mL of water and dried, thereby giving 1.93 g of 6-chloro-3-(ethylsulfonyl)pyridine-2-carboxamide.

$^1$H-NMR (DMSO-$d_6$) δ: 8.34 (1H, d), 8.26 (1H, s), 7.98 (1H, s), 7.89 (1H, d), 3.63 (2H, q), 1.16 (3H, t).

Example 3

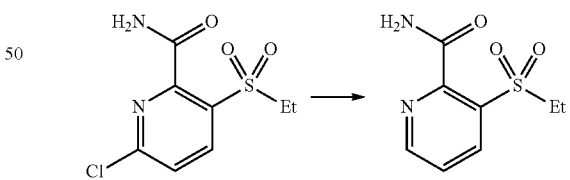

Under a nitrogen atmosphere, 50 mg of Pd/C (Pd loading: 5 wt %, water content: 61 wt %) was added to a mixture of 0.33 g of sodium acetate, 3.2 g of methanol, and 1.0 g of 6-chloro-3-(ethylsulfonyl)pyridine-2-carboxamide and stirred at 40° C. for 3 hours under a hydrogen atmosphere. After purging with nitrogen, Pd/C was filtered, and Pd/C was washed with a mixed solution of 10 g of acetonitrile and 10 g of water. A solution combining the filtrate and the washing liquid was analyzed by liquid chromatography. As a result, it was confirmed that 0.87 g of 3-(ethylsulfonyl)pyridine-2-carboxamide was contained.

$^1$H-NMR (DMSO-$d_6$) δ: 1.12-1.16 (3H, t), 3.63-3.69 (2H, q), 7.75-7.78 (1H, m), 7.84 (1H, br), 8.16 (1H, br), 8.32-8.35 (1H, m), 8.85-8.87 (1H, m)

Example 4

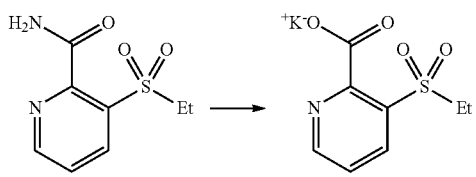

Under a nitrogen atmosphere, 1.00 g of 3-(ethylsulfonyl)pyridine-2-carboxamide was added to a mixture of 2.36 g of 2-propanol, 1.00 g of water, and 0.34 g of potassium hydroxide at room temperature, heated to 80° C., and stirred for 10 hours. The reaction mixture was concentrated at 40° C. under reduced pressure, and 1.00 g of 2-propanol was added and further concentrated at reduced pressure. To the concentrate, 1.00 g of methanol was added and heated to 70° C. to dissolve, and 2.56 g of toluene was added, followed by cooling to 0° C. Further, 2.50 g of toluene was added at 0° C., the precipitate was filtered, and the obtained solid was washed with 1.58 g of toluene. The obtained solid was dried under reduced pressure, thereby giving 0.90 g of potassium 3-(ethylsulfonyl)-2-carboxylate (purity: 87.1%).

$^1$H-NMR (DMSO-$d_6$) δ: 1.03-1.07 (3H, t), 3.70-3.75 (2H, q), 7.38-7.41 (1H, m), 8.06-8.09 (1H, m), 8.61-8.64 (1H, m)

Example 5

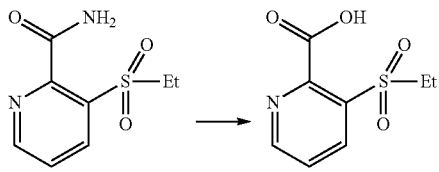 [SMILES: CCS(=O)(=O)c1cccnc1C(N)=O ; CCS(=O)(=O)c1cccnc1C(=O)O]

Under a nitrogen atmosphere, 3.00 g of 93.1 wt % 3-(ethylsulfonyl)pyridine-2-carboxamide was added to a mixture of 6.59 g of 2-propanol, 2.79 g of water, and 0.94 g of 85.5 wt % potassium hydroxide at room temperature, heated to 80° C., and stirred for 11 hours. Further, 0.09 g of 85.5 wt % potassium hydroxide was added and stirred at the same temperature for 7 hours. The reaction mixture was cooled to 0° C., 1.75 g of 35 wt % hydrochloric acid was added dropwise, and the precipitated solid was filtered. The obtained solid was washed with 2.79 g of 2-propanol and dried, thereby giving 1.96 g of 3-(ethylsulfonyl)pyridine-2-carboxylic acid.

$^1$H-NMR (DMSO-$d_6$) δ: 1.15-1.19 (3H, t), 3.49-3.55 (2H, q), 7.79-7.83 (1H, m), 8.35-8.38 (1H, m), 8.90-8.92 (1H, m)

Comparative Example 1

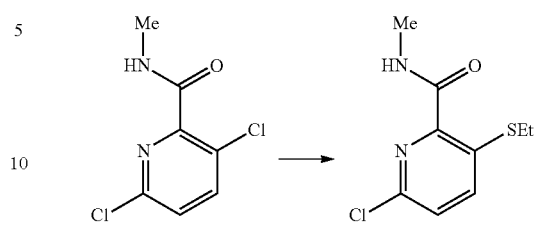

To a mixture of 100 mg of N-methyl-3,6-dichloropyridine-2-carboxamide and 500 μL of toluene, 170 μL of a mixture of 9.78 g of 28 wt % sodium methoxide and 3.00 g of ethanethiol was added dropwise at room temperature. The reaction mixture was stirred at room temperature for 7 hours, thereby giving N-methyl-6-chloro-3-(ethylthio)pyridine-2-carboxamide with a liquid chromatography area percentage of 62.6% and N-methyl-3-chloro-6-(ethylthio)pyridine-2-carboxamide with a liquid chromatography area percentage of 7.3%.

$^1$H-NMR (CDCl$_3$) δ: 7.80 (1H, s), 7.61 (1H, d), 7.34 (1H, d), 3.00 (3H, d), 2.89 (2H, q), 1.40 (3H, t)

Like this, in an N-methylamide compound, the substitution reaction of the chlorine atom at 3-position of 3,6-dichloropyridine-2-carboxylic acid did not progress in good yield.

Comparative Example 2

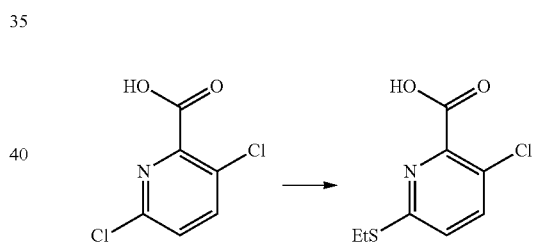

Under a nitrogen atmosphere, 35.5 mg of ethyl mercaptan was added to a mixture of 100 mg of 3,6-dichloropyridine-2-carboxylic acid, 45.7 mg of sodium hydride (content: 60%), and 1 mL of tetrahydrofuran at room temperature and stirred at 40° C. for 2 hours. The reaction mixture was analyzed by liquid chromatography. As a result, 6-chloro-3-(ethylthio)pyridine-2-carboxylic acid was not formed, and 3-chloro-6-(ethylthio)pyridine-2-carboxylicacid was formed with an area percentage of 10%.

Like this, the substitution reaction of the chlorine atom at 3-position of 3,6-dichloropyridine-2-carboxylic acid, which is not an amide compound, did not progress in good yield, and only the substitution reaction of the chlorine atom at 6-position slightly progressed.

INDUSTRIAL APPLICABILITY

According to the method of the present invention, a compound useful as an intermediate in the production of pharmaceuticals and agrochemicals, such as 3-(alkylsulfonyl)pyridine-2-carboxylic acid, can be produced.

The invention claimed is:
1. A method for producing a compound represented by formula (7) or a salt thereof, comprising:
   a step of allowing a compound represented by formula (1-N):

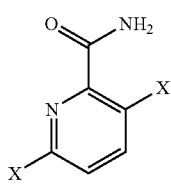

(1-N)

wherein X represents a halogen atom,
to react with a compound represented by formula (2):

$$R^2SM^2 \quad (2)$$

wherein $R^2$ represents a $C_{1-8}$ straight-chain alkyl group, and $M^2$ represents a hydrogen atom or an alkali metal,
to give a compound represented by formula (3-N):

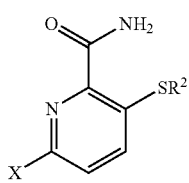

(3-N)

wherein $R^2$ and X are as defined above;
a step of allowing the compound represented by formula (3-N) to react with hydrogen peroxide in the presence of a tungsten catalyst and an acid to give a compound represented by formula (6-N):

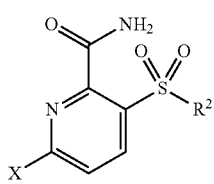

(6-N)

wherein $R^2$ and X are as defined above;
a step of reducing the compound represented by formula (6-N) in the presence of a base and a heterogeneous transition metal catalyst to give a compound represented by formula (8-N):

(8-N)

wherein $R^2$ is as defined above; and
a step of hydrolyzing the compound represented by formula (8-N) in the presence of a base to give a compound represented by formula (7) or a salt thereof:

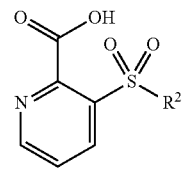

(7)

wherein $R^2$ is as defined above.

2. A method for producing a compound represented by formula (8-N), comprising:
   a step of allowing a compound represented by formula (1-N):

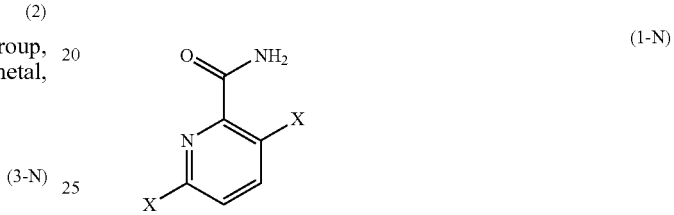

(1-N)

wherein X represents a halogen atom,
to react with a compound represented by formula (2):

$$R^2SM^2 \quad (2)$$

wherein $R^2$ represents a $C_{1-8}$ straight-chain alkyl group, and $M^2$ represents a hydrogen atom or an alkali metal,
to give a compound represented by formula (3-N):

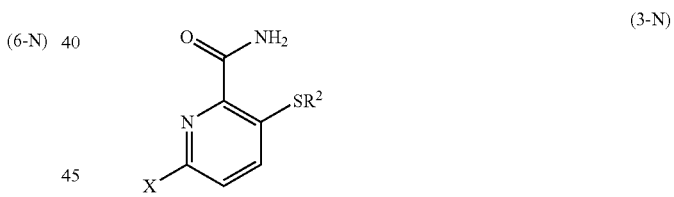

(3-N)

wherein $R^2$ and X are as defined above;
a step of allowing the compound represented by formula (3-N) to react with hydrogen peroxide in the presence of a tungsten catalyst and an acid to give a compound represented by formula (6-N):

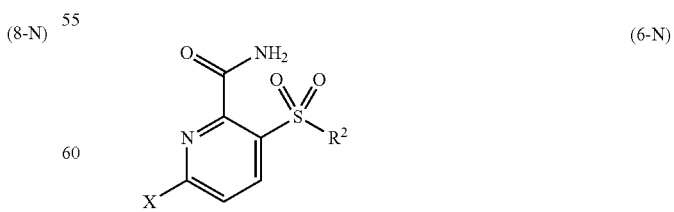

(6-N)

wherein $R^2$ and X are as defined above; and
a step of allowing the compound represented by formula (6-N) to react in the presence of a base and a heterogeneous transition metal catalyst to give a compound represented by formula (8-N):

(8-N)

wherein R² is as defined above.

3. A method for producing a compound represented by formula (6-N), comprising:

a step of allowing a compound represented by formula (1-N):

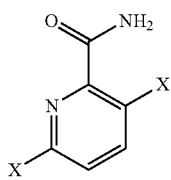

(1-N)

wherein X represents a halogen atom,
to react with a compound represented by formula (2):

$$R^2SM^2 \qquad (2)$$

wherein R² represents a C$_{1-8}$ straight-chain alkyl group, and M² represents a hydrogen atom or an alkali metal, to give a compound represented by formula (3-N):

(3-N)

wherein R² and X are as defined above; and
a step of allowing the compound represented by formula (3-N) to react with hydrogen peroxide in the presence of a tungsten catalyst and an acid to give a compound represented by formula (6-N):

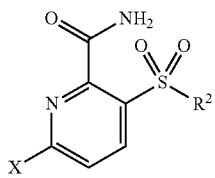

(6-N)

wherein R² and X are as defined above.

4. A method for producing a compound represented by formula (3-N), comprising a step of allowing a compound represented by formula (1-N):

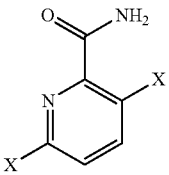

(1-N)

wherein X represents a halogen atom,
to react with a compound represented by formula (2):

$$R^2SM^2 \qquad (2)$$

wherein R² represents a C$_{1-8}$ straight-chain alkyl group, and M² represents a hydrogen atom or an alkali metal, to give a compound represented by formula (3-N):

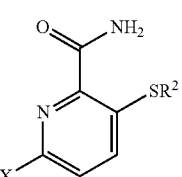

(3-N)

wherein R² and X are as defined above.

5. A compound represented by formula (3-N):

(3-N)

wherein R² represents a C$_{1-8}$ straight-chain alkyl group, and X represents a halogen atom.

6. A compound represented by formula (6-N):

(6-N)

wherein R² represents a C$_{1-8}$ straight-chain alkyl group, and X represents a halogen atom.

* * * * *